(12) United States Patent
Lavi

(10) Patent No.: US 9,980,759 B2
(45) Date of Patent: May 29, 2018

(54) INTRAMEDULLARY NAIL AND NAIL COMBINATIONS

(75) Inventor: Abraham Lavi, Lakewood Ranch, FL (US)

(73) Assignee: Vilex in Tennessee, Inc., McMinnville, TN (US)

( * ) Notice: Subject to any disclaimer, the term of this patent is extended or adjusted under 35 U.S.C. 154(b) by 0 days. days.

(21) Appl. No.: 13/608,732

(22) Filed: Sep. 10, 2012

(65) Prior Publication Data

US 2013/0245626 A1   Sep. 19, 2013

(51) Int. Cl.
*A61B 17/56* (2006.01)
*A61B 17/58* (2006.01)
*A61F 2/30* (2006.01)
*A61B 17/72* (2006.01)
*A61B 17/86* (2006.01)

(52) U.S. Cl.
CPC .......... *A61B 17/72* (2013.01); *A61B 17/7225* (2013.01); *A61B 17/863* (2013.01); *A61B 17/8685* (2013.01)

(58) Field of Classification Search
CPC .......................... A61B 17/8625; A61B 17/863

USPC ........... 606/264–275, 62, 300–321, 95, 105; 411/411–415, 420
See application file for complete search history.

(56) References Cited

U.S. PATENT DOCUMENTS

| 8,303,634 | B2 * | 11/2012 | Martin | .......................... 606/317 |
| 2007/0297871 | A1 * | 12/2007 | Lu | ....................... F16B 25/0015 411/387.1 |
| 2008/0031705 | A1 * | 2/2008 | Severns | ................ F16B 5/0275 411/413 |
| 2012/0232599 | A1 * | 9/2012 | Schoenly | ........... A61B 17/8635 606/315 |
| 2012/0265258 | A1 * | 10/2012 | Garvey | ........................ 606/315 |

* cited by examiner

*Primary Examiner* — Ellen C Hammond
*Assistant Examiner* — Christina Negrellirodrigue
(74) *Attorney, Agent, or Firm* — Barbara E. Johnson, Esq.

(57) ABSTRACT

The present bone implant is a cannulated screw/nail or combination having end, middle and head threads as well as unthreaded portions along the length of the shaft. The pitch of the head threads is always less than the middle threads. Variations include a two-part construction with a narrow protrusion having narrow-protrusion threads of opposite hand, or the inclusion of at least first middle threads and second middle threads of different pitch. The implant provides bone compression engineering heretofore unavailable with prior known compression screws.

10 Claims, 4 Drawing Sheets

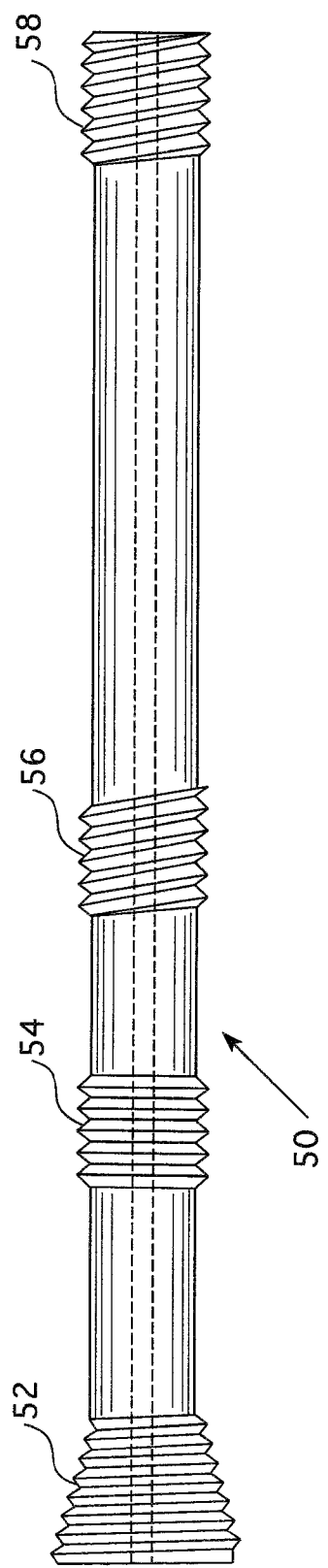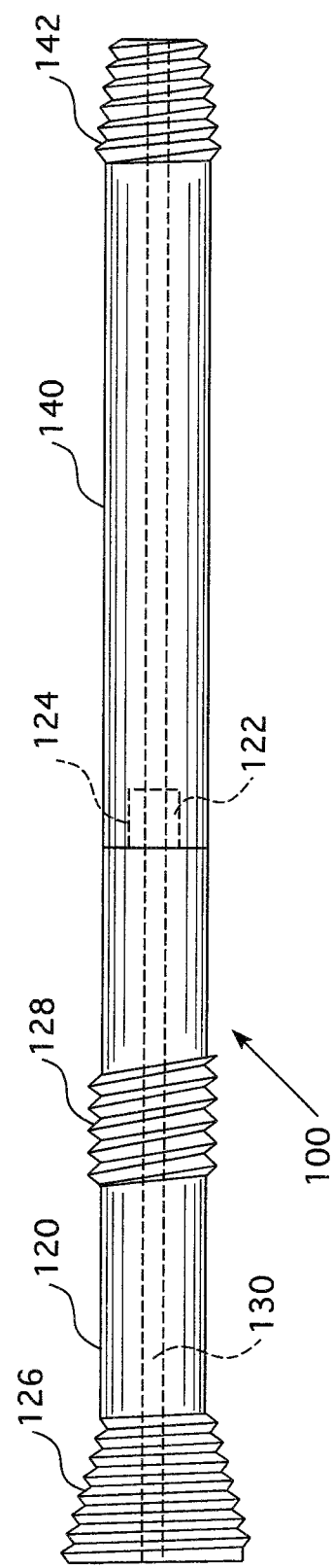
FIG. 3
FIG. 4

INTRAMEDULLARY NAIL AND NAIL COMBINATIONS

CROSS-REFERENCE TO RELATED APPLICATIONS

This patent application claims priority to, and incorporates herein by reference in entirety, U.S. Provisional Patent Application No. 61/532,374 filed Sep. 8, 2011.

BACKGROUND OF THE INVENTION

Field of the Invention

The present invention relates to intramedullary nails, nail combinations, and bone screws for tibiotalo fusion and talo-calcaneal fusion or distraction as desired. The implant contains particular threading and diameter configurations to achieve selectively both fusion or distraction of the ankle joint within the bare foot.

Description of Related Art

Dual-thread screws, also known as Herbert screws, are known in the art and include end threads as well as head threads, with the head threads having a finer pitch than the end threads. Such a dual-thread screw functions as a compression screw to fixate bone fractures and to fuse joints. A conventional dual-thread screw is shown in FIG. 1. Dual thread screws can be solid or cannulated. Intramedullary nails are known in the art and consist of a solid rod inserted inside a long bone, e.g., the tibia or a metatarsal shaft, and with variously oriented holes for fixating the rod to the host bone. However, conventional compression screws exert compression over the entire length of the shaft, leaving a need for intramedullary nail and screws combinations that provide for more particularly engineered compression.

SUMMARY OF THE INVENTION

The present bone implant is one of three embodiments of a cannulated screw (or screw/nail) having at least end, middle and head threads and, in one embodiment, both first and second middle threads. In the first embodiment, the end and middle threads possess identical pitch, and the construct is hereafter referred to as the "first implant". The middle and end threads of the first implant are synchronized and follow an identical pattern. However, the end diameter is slightly less than the middle diameter, with the end threads diameter being approximately 1-10%, preferably 1-5%, smaller than the middle threads diameter, and the tip of the end is sharpened, enabling it to drill and tap as it advances. The tip diameter may be between 10% to 80% of the diameter of the widest diameter of the end threads. The head thread has a finer pitch (50-60% less pitch) than the remainder of the bone screw; the pitch of the end and middle threads is virtually always if not always the same. The first implant affords stable and load-sharing internal fixation. In order to fixate the first implant to the host bone and achieve the attributes of an intramedullary nail, Lateral-Medial (L-M) and Posterior-Anterior (P-A) holes are drilled appropriately along the length for the insertion of locking screws to secure the implant to the host bone and to prevent rotation. Thus, the shape is a cannulated rod (tube), made from biocompatible stainless steel, cobalt chrome, or titanium alloy with holes for locking cross screws that provide rotational stability and load distribution. The first implant holes may be straight or angled relative to the longitudinal axis of the implant. The resultant first implant device is the integration of a compression screw, conventional or dual-thread, and an intramedullary nail. The screw aspects of the implant provide compression across one or more bone joints and the nail aspects with the holes provide both stability and load distribution along the bone columns. It is necessary to provide the implant in different diameters and lengths to match patient anatomy and bone condition. Special instruments are necessary to drill and ream the bone and to compress the arthrodesis site. A special targeting device locks into the implant for the insertion of the locking cross screws.

The second embodiment (second implant) is a variation on the first implant, in that both first middle threads and second middle threads are present. The first middle threads, nearest the head threads, have a smaller pitch than the second middle threads. The second middle threads have the same or approximately the same pitch as the end threads, whereas the head threads have a pitch in between the first middle and second middle threads. As described further below, the four sets of threads having the stipulated relatively different pitch enable selective compression of the adjacent bone between the first and second middle threads and distraction of the adjacent bone between the head threads and the first middle threads. Typically, the head threads engage calcaneous bone whereas the first middle threads engage the talus and the second middle threads engage the tibia. The end threads and the second middle threads are synchronized and follow an identical pattern.

The third embodiment (third implant) is a three-piece structure having certain similarities and differences with respect to the first implant and the second implant. Basically, the third embodiment of the invention embraces a two-part intramedullary nail combination having a head part and end part, in which the head part contains a narrow protrusion having opposite-direction threads thereon designed to engage the end part and wherein the entire combined two-part intramedullary nail contains a threaded cannula throughout its length designed to receive a threaded locking wire and perforating centrally and annularly to the parts including the narrow protrusion.

BRIEF DESCRIPTION OF THE DRAWING(S)

FIG. 3 is a sectional view of the second implant.

FIG. 4 is a sectional view of the third implant.

DETAILED DESCRIPTION OF THE INVENTION

Figure 1:
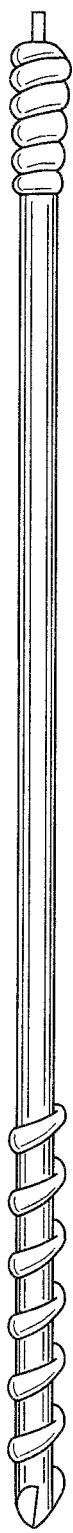
FIG. 1 is a side elevational view of a prior art bone screw.

Referring now to the first embodiment, the present first implant is a cannulated screw having end, middle and head threads. The end and middle threads possess identical or approximately identical pitch as well as pattern, that is, the middle and end threads are synchronized and follow an identical pattern beyond merely having identical pitch. This is important so that when the middle thread reaches the distal tibia or other bone insertion location, the middle threads will follow the grooves made first by the end threads. Without synchronization, the middle threads will drill and tap their own pattern even if the pitch is unchanged between the middle and end threads. However, the end diameter is slightly less (approximately 1-10%, preferably 1-5% smaller) than the middle diameter and the tip of the end is sharpened so that it can drill and tap as it advances. The head thread has a finer pitch (50-60% less pitch) than the remainder of the implant; the pitch of the end and middle threads is virtually always if not always the same for the reasons explained above. The first implant affords stable and load-sharing internal fixation. The shape is a cannulated rod (tube), made from biocompatible stainless steel, cobalt chrome, or titanium alloy with Lateral-Medial (L-M) and Posterior-Anterior (P-A) holes for locking cross screws that provide rotational stability and load distribution. It is necessary to provide the first implant in different diameters and lengths to match patient anatomy and bone condition. Special instruments are necessary to drill and ream the bone and to compress the arthrodesis site. A special targeting device locks into the first implant head for the insertion of the locking cross screws.

The above-described first implant, particularly a tibiotalocalcaneal ankle fusion application, may be surgically implanted as follows. The surgeon exposes the arthrodesis site, removes the cartilage surgically, and prepares it for fusion. After appropriate tissue dissection, the surgeon drives a 2.0-3.0 mm guide wire, preferably a guide wire 2.5 mm in diameter, from the base of the calcaneous below the talus and extending inward toward the ankle from the bottom (sole) of the foot. In tibiotalocalcaneal ankle fusion, the guide wire is first advanced to the talo-tibial interface. The surgeon then aligns the tibia center with the guide wire in the desired position, and advances the wire into the intramedullary canal. At this stage, the surgeon compresses the joint(s) either manually or preferably using a special monorail that is designed to attach to the targeting device. The monorail is used both to close any gap between the joint bones and to compress the joint. The monorail should be sufficiently long so as not to interfere with the guide wire or the first implant when inserted. The half pins of the monorails should be positioned in the upper tibia and mid-foot bones to insure axial compression of the joint and to avoid the creation of a twisting torque. It is essential that the gap is closed prior to the insertion of the first implant. Using a cannulated drill having a diameter smaller than the smooth shaft diameter of the first implant, the surgeon drills a path for the first implant from the calcaneous through the distal tibia. An appropriate cannulated reamer clears the path of the first implant further. The first implant is then chosen having a diameter matching the prepared (reamed) bone diameter and is inserted and manually advanced using an appropriate screwdriver. The leading end is capable of further drilling the bone to advance and to tap its way due to its sharpened tip and relatively narrow diameter. When the middle thread engages the distal end of the tibia, the middle threads cut deeper into the bone than did the narrower leading end threads. The presence of threads in the tibia does not introduce any longitudinal (axial) stress forces along the tibia because the pitch of the thread embedded within the tibia is uniform throughout, both as to the end and middle threads. When the first implant head engages the plantar aspect of the calcaneous, it threads the bone with the finer pitch of the head thread. The main thread pitch is 2.5-3.0 mm and the head thread pitch is 1.5-1.7 mm. This means that the tibiotalocalcaneal joints close at the rate of approximately 1.0 mm per turn of the first implant. With a 10.0 mm head thread length, the potential compression is (9*1.00/1.5) =~6.0 mm. The maximum compression is achieved if tibiotalocalcaneal gaps are manually closed prior to advancing the first implant. The compression force materializes only if the bone is sufficiently dense where the first implant head is embedded in the calcaneous and also where the middle thread is embedded in the tibia. If the middle thread does not clear the talus and is not confined to the tibia, only the talo-calcaneal joint is compressed.

Figure 2:
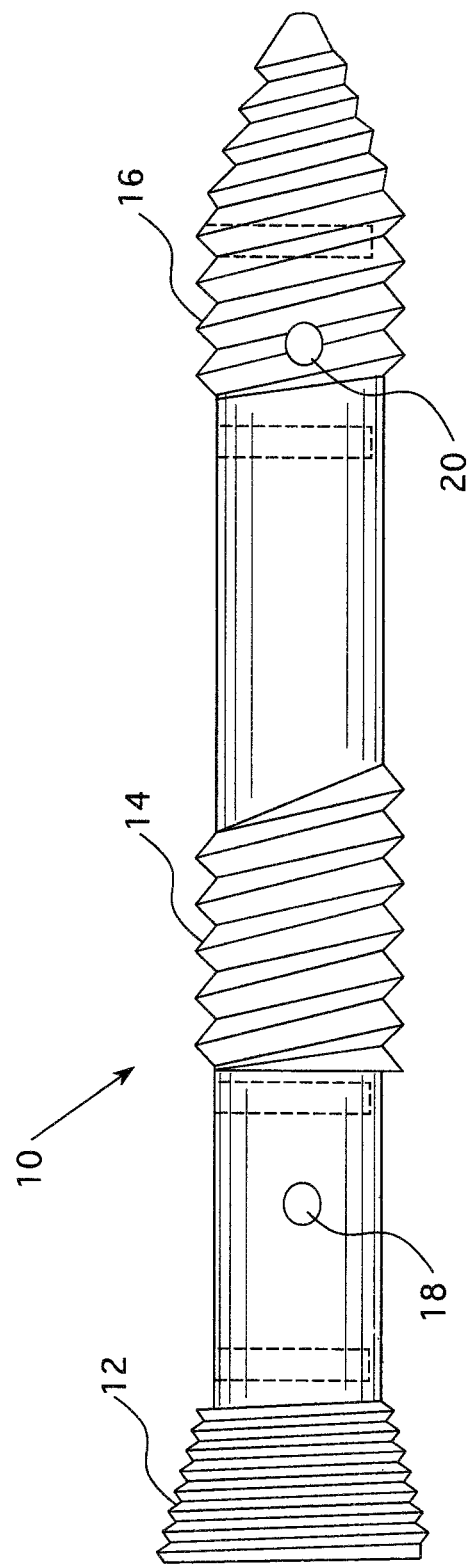
FIG. 2 is a side elevational view of the first implant.

FIG. 2 illustrates the position and orientation of the locking holes relative to the thread positions. The first implant according to the invention preferably has a minimum of six holes with four extending in the lateral-medial direction, one posterior-anterior hole between the head and middle threads and one posterior-anterior hole being positioned on or near the trailing portion of the end threads. The hole between the head and middle threads is slanted 45 degrees and is positioned to clear the tibia, that is, to be in position such that the portion of the shaft of the first implant on which the slanted hole is positioned does not extend into the tibia. A locking screw through this hole will compress the talo-calcaneal joint. This locking screw may be inserted anterior-posterior, or after drilling the bone the drill or Steinman is advanced until it exits the heel and the locking screw is then inserted from the heel, through the 45-degree hole and into the talus. The proximal anterior-posterior hole is also slanted about 10 degrees so that the locking screw is embedded at an angle. Separate locking screws may also be inserted in some or all of the other above-described holes in the present first implant.

The first implant of the present invention may have different thread diameters and lengths. Ideally, the middle thread should clear the talus after implantation, that is, the middle threads should extend completely into the distal tibia. The location of the middle thread varies in order to accommodate variability in foot anatomy and dimensions. Using a pre-operative x-ray of the leg, and considering the weight of the patient and the diameter of the tibia, the surgeon first selects the first implant diameter, and then decides on the length of the first implant and the position of the middle thread. The shortest length of the inventive first implant (namely, 150 mm) should be reserved to trauma cases where a longer first implant cannot be fixated proximally due to damage to the tibia. Generally a longer first implant is preferred over a shorter one. The length of the middle threads is generally 15-40%, more preferably 15-30%, of the length of the first implant as a whole.

Implantation of the present first implant may be accomplished with guides and tools designed specifically to work together as a system. The screwdriver is designed to lock into the head of the first implant in a well-defined orientation and thus can the screwdriver-implant combination be locked into the targeting device in only one orientation. The external monorail and the targeting device can be fixated to each other in a manner to provide compression and to avoid interference with the implantation process of the screw/nail implant (first implant).

Although the bulk of the above discussion and illustration is focused on tibiotalocalcaneal ankle fusion, the same concept and implant can be utilized in other joint configurations in the hand and foot. The invention can be used, for example, in the fusion of the metatarsal-cuneiform-navicular-calcaneus column. The first implant diameter for this purpose should be reduced to no greater than 8.0 mm and the locking screws reduced in size accordingly. A different targeting tool will be necessary as well. However, the required changes are straightforward. As long as the first implant head is embedded in high density bone and the middle thread is embedded in bone segment as well, one or more joints removed (that is, adjacent), the subject invention is surgically and medically effective.

Referring again to FIG. 2, the first implant 10 has head threads 12, middle threads 14 and end threads 16, as well as posterior-anterior holes 18 and 20. These structures have already been discussed immediately above.

Referring now to FIG. 3, the second implant (second embodiment) of the invention 50 has head threads 52, first middle threads 54, second middle threads 56 and end threads 58. The head threads 52 have a pitch in between the pitch of the first middle threads 54 and the second middle threads 56, and the first middle threads 54 have a smaller pitch than the second middle threads 56. The second middle threads 56 have the same or approximately the same pitch as the end threads 58. These four sets of threads having the stipulated relatively different pitch enable selective compression of the engaged bone between the first and second middle threads 54, 56 and distraction of the engaged bone between the head threads 52 and the first middle threads 54. Typically, the head threads 52 engage calcaneous bone whereas the first middle threads engage the talus and the second middle threads engage the tibia. Sample pitches for the purpose of illustration, not limitation, are head threads 52 1.75 mm/10 mm, first middle threads 54 1.5 mm/10 mm, second middle threads 56 2.75 mm/10 mm and end threads 58 2.75 mm/15 mm. In the previous notations, the "slash" refers to the length of the thread, so 2.5 mm/15 mm means the pitch is 2.5 mm and the thread length is 15 mm which, as 15/2.5, means a total of six threads.

Figure 5:
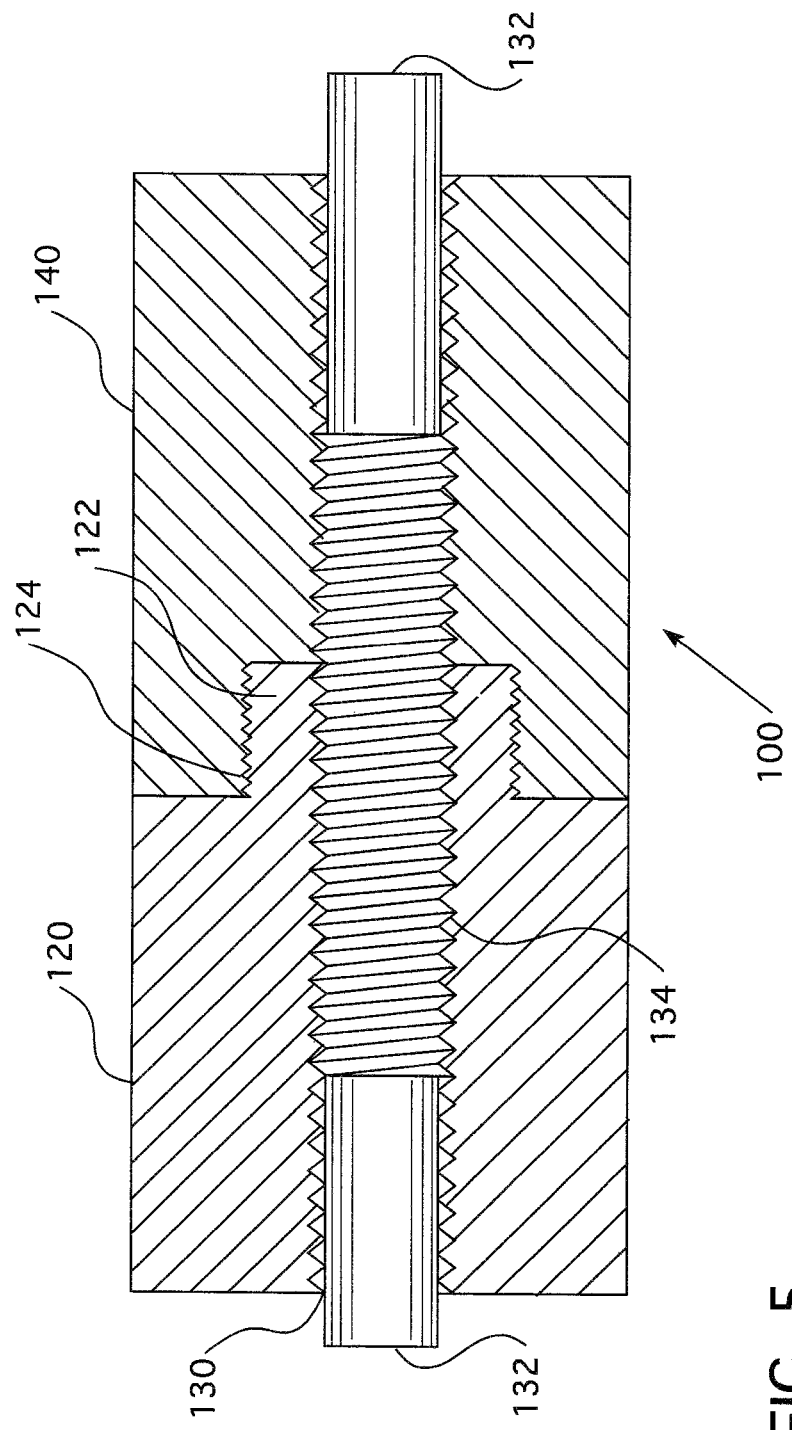
FIG. 5 is a sectional view of a portion of the third implant, shown not to scale, to show the detail of the narrow protrusion of the head end and the threads thereon, as well as the threaded cannulation extending throughout the combination including through the protrusion, as well as the locking wire which engages the threaded cannulation.

The third embodiment of the invention is illustrated in pertinent part in FIGS. 4-5. The third implant is a nail/screw combination 100 having a head part 120 and an end part 140 having end threads 142. The head part 120 has head threads 126, middle threads 128 and a narrow protrusion 122 having narrow protrusion threads 124. The end part 140 has a threaded cavity to mate with the narrow protrusion 122 and its narrow protrusion threads 124. The narrow protrusion threads 124 have opposite handedness to all other threads throughout the combination, so if all but one of the nail/screw combination 100 threads are right-handed threads, the narrow protrusion threads 124 will be left-handed. Likewise, if the narrow protrusion threads 124 are right-handed, then all other threads in the nail/screw combination 100 are left-handed. Referring now to FIG. 5, the details not visible in FIG. 4 are illustrated (not to scale). The narrow protrusion 122 and the associated head part 120 may be seen as annularly perforated throughout by a threaded cannulation 130 which extends through the end part 140. Removably disposed within the threaded cannulation 130 is locking wire 132, which is threaded along only an adequate portion of its length so as to engage a portion of both the head part/narrow protrusion 120,122 as well as the end part 140. The narrow protrusion threads 124 have a very fine pitch, such as for example 0.75 mm, whereas the head threads have a pitch lesser than the pitch of the middle threads. Recall that the narrow protrusion threads 124 are opposite-handed to the head or middle threads 126, 128. In operation, when the entire nail/screw combination 100 is held together by the locking wire 132, the head part 120 and the end part 140 form a single interlocked piece. With the locking wire 132 in place, the nail/screw combination 100 can be screwed into position in the desired bone or bones by means known in the art, such as with a driver or screwdriver. However, when the nail/screw combination 100 is in position, fine tuning of compression of the encompassing bone or bones may be engineered by removing the threaded locking wire, second by locking the leading end to the host bone, and then continuing to drive or rotate the nail/screw combination 100 a few or several more turns into final position. During such further rotation, compression of adjacent bone occurs between the head threads 126 and the middle threads 128, whereas due to the opposite-handed threads of the narrow protrusion 122, the narrow protrusion 122 gradually disengages the head part 120 from the end part 140 and thus distracts the immediately adjacent bone. This final positioning can be particularly beneficial if, for example, the surgeon wants to compress certain bones in the foot but distract the bones of the ankle joint. Conversely, when it is time to remove the entire third implant after all bones have healed and regrown, the surgeon replaces the locking wire and thus is able to extract the entire third embodiment implant by counter-rotating it, that is, by rotating it in the opposite direction as was used for implantation. The pitches of the head threads 126 and middle threads 128 can vary anywhere from 1 mm/10 to 3 mm/10 as long as the head threads 126 have a smaller pitch than the middle threads 128. The narrow protrusion threads 124 are always relative fine in pitch and can range from 0.5 mm up to about 1 mm. The locking wire 132 will generally have a threaded portion extending between about 1 cm to 4 cm, preferably about 2-3 cm along a central portion of its length. The threads of the locking wire 132 are always opposite-handed to the hand of the narrow protrusion threads 124.

Implantation of the second and third embodiments of the invention is accomplished basically the same way as described above for the first embodiment. Drill guides, guide wires, reaming and advancement of the implants are all accomplished by means known in the art.

The invention claimed is:

1. A bone implant for tibiotalo fusion or talo-calcaneal fusion or distraction comprising a bone screw having an end, a middle and a head, which each of said end, middle and head have threads comprising end threads, middle threads and head threads wherein said end threads and said middle threads are separated by an unthreaded expanse of said implant, further wherein said head threads have a finer pitch than said middle threads, further wherein said end threads are substantially or completely continuous and have a largest diameter 1-10% less than the largest diameter of said middle threads and further wherein the end threads and the middle threads have the same pitch and are synchronized, whereby said middle threads and said end threads have the same pitch and pattern and thus follow an identical pattern upon insertion, further wherein the length of the middle threads is 15-40% of the length of the screw as a whole, further wherein the head threads have a diameter greater than the middle threads, and further wherein a posterior-anterior hole is present between said head threads and said middle threads wherein said posterior-anterior hole is slanted 45 degrees into said bone screw.

2. The bone implant according to claim 1, wherein the pitch of the head threads is about 50-60% finer than the pitch of the middle threads.

3. The bone implant according to claim 2, wherein the length of the middle threads is 15-30% of the length of the screw as a whole.

4. The bone implant according to claim 3 wherein all threads are cutting threads.

5. The bone implant according to claim 4 wherein the end threads have a largest diameter which is 1-5% less than the largest diameter of the middle threads.

6. The bone implant according to claim 1 wherein the bone screw is cannulated.

7. The bone implant according to claim 5 wherein at least one additional hole is positioned in said screw, said hole being adapted to receive a locking screw.

8. The bone implant according to claim 7 wherein said implant is fabricated in two pieces comprising a head part and an end part, wherein said head part and said end part are interconnected by either or both of a narrow protrusion on said head part and a threaded locking wire of engageable dimensions relative to a threaded cannula throughout the length of the implant.

9. The bone implant according to claim 8 wherein threads on said narrow protrusion have opposite handedness to all other threads throughout said implant.

10. The bone implant according to claim 9 wherein said threaded locking wire is threaded only along a central portion of its length.

\* \* \* \* \*